United States Patent [19]

Ikegawa et al.

[11] Patent Number: 5,476,945
[45] Date of Patent: Dec. 19, 1995

[54] WATER-SOLUBLE METHINE DERIVATIVES OF THIAZOLE

[75] Inventors: Akihiko Ikegawa; Toshinao Ukai; Masayuki Kawakami, all of Kanagawa, Japan

[73] Assignee: Fuji Photo Film Co., Ltd., Kanagawa, Japan

[21] Appl. No.: 138,061

[22] Filed: Oct. 19, 1993

[30] Foreign Application Priority Data

Nov. 17, 1992 [JP] Japan ................................. 4-304769

[51] Int. Cl.⁶ ........................ C07D 417/14; C07D 413/14
[52] U.S. Cl. ........................ 548/152; 548/150; 548/156; 548/159; 546/274; 546/280; 544/284; 544/333
[58] Field of Search ........................ 548/152, 150, 548/156, 159; 546/280, 274; 544/333, 284

[56] References Cited

U.S. PATENT DOCUMENTS 2,388,963  11/1945  Fry et al. ........................ 260/240

*Primary Examiner*—David B. Springer
*Attorney, Agent, or Firm*—Sughrue, Mion, Zinn, Macpeak & Seas

[57] ABSTRACT

A methine compound represented by the following formula (I):

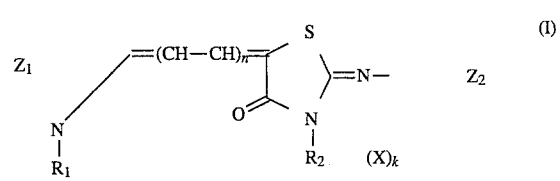

wherein $Z_1$ and $Z_2$ each represent a non-metallic atomic group necessitated for forming a five-membered or six-membered, nitrogen-containing heterocyclic ring, $R_1$ and $R_2$ each represent an alkyl group, X represents an inorganic anion, k represents a number necessitated for adjusting the electric charge of the molecule to zero, and n represents 0 or 1; with the proviso that when n is 1, the five-membered or six-membered, nitrogen-containing heterocyclic ring formed by $Z_2$ is cationic, k is not zero and X represents chloride ion. The compound is useful as a spectral sensitizing dye and an antitumor agent.

7 Claims, No Drawings

WATER-SOLUBLE METHINE DERIVATIVES OF THIAZOLE

BACKGROUND OF THE INVENTION

The present invention relates to methine compounds useful as photographic materials, medicines and the like.

In the field of photographic science, the methine compounds of the present invention belong to materials useful as spectral sensitizing dyes like compounds described in, for example, U.S. Pat. Nos. 2,388,963, 2,454,629, 2,927,630, 3,979,213 and 3,796,733, French Patent Nos. 2,117,337 and 1,486,987 and West German Patent No. 2,120,323. In particular, the methine compounds of the present invention belong to so-called rhodacyanine dyes. However, by replacing the methine chain of these compounds with nitrogen atom, the absorption wavelength of them becomes shorter than that of the ordinary rhodacyanines. Therefore, these compounds are effectively useful when a spectral absorption sensitivity at a wavelength shorter than that of ordinary rhodacyanines is necessitated. Although rhodacyanines having a nitrogen atom in place of the methine chain have been already disclosed in, for example, U.S. Pat. No. 2,388,963, the solubility of these compounds is poor, which poses a problem when they are incorporated into a photograhic emulsion.

On the other hand, also in medical and pharmaceutical fields, it has been found that the compounds of the present invention are usable as medicines such as antitumor agents. However, also in these fields, short absorption wavelengths of solutions of them or, in other words, the solutions having a light color are preferred, since they do not make the patients feel uneasy. Also in these fields, the solubility is an important problem. In particular, the methine compounds should not be precipitated or aggregated in a medium having a high salt concentration such as blood in a living body.

Thus the color tone and solubility of the compounds are important points in both fields.

SUMMARY OF THE INVENTION

Therefore, a primary object of the present invention is to provide methine compounds having an absorption at a wavelength shifted to shorter side and an excellent solulbility.

This and other objects of the present invention will be apparent from the following description and examples.

The object of the present invention can be attained by using a methine compound of the following general formula (I):

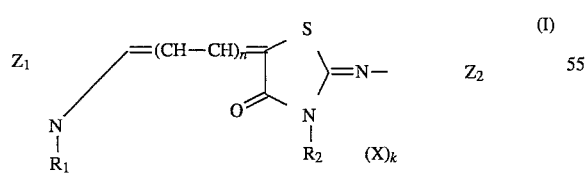

wherein $Z_1$ and $Z_2$ each represent a non-metallic atomic group necessitated for forming a five-membered or six-membered, nitrogen-containing heterocyclic ring, $R_1$ and $R_2$ each represent an alkyl group, X represents an inorganic anion, k represents a number necessitated for adjusting the electric charge of the molecule to zero, and n represents 0 or 1; with the proviso that when n is 1, the five-membered or six-membered, nitrogen-containing heterocyclic ring formed by $Z_2$ is cationic, k is not zero and X represents chloride ion.

DESCRIPTION OF THE PREFERRED EMBODIMENT

The alkyl groups herein are those having preferably 1 to 5 carbon atoms, more preferably 1 to 3 carbon atoms.

The methine compounds represents by the general formula (I) are preferably those represented by the following general formula (II), (III) or (IV):

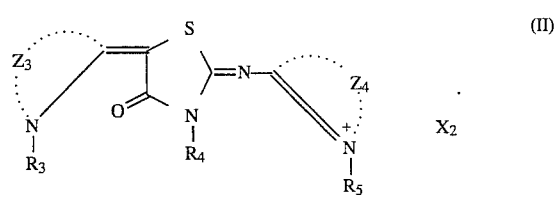

wherein $Z_3$ represents a non-metallic atomic group necessitated for forming a thiazolidine ring, thiazoline ring, benzothiazoline ring, tetrahydrobenzothiazoline ring, naphthothiazoline ring, dihydroquinoline ring or dihydropyridine ring, $Z_4$ represents a non-metallic atomic group necessitated for forming a pyridinium ring, thiazolium ring, pyrimidinium ring, benzothiazolium ring, quinolinium ring or naphthothiazolium ring, $R_3$, $R_4$ and $R_5$ each represent an alkyl group having 3 or less carbon atoms and $X_2$ represents an inorganic anion.

In particular, the heterocyclic ring represented by $Z_3$ is more preferably a benzothiazoline ring, naphthothiazoline ring or dihydroquinoline ring. The heterocyclic ring represented by $Z_3$ may have a substituent. Preferred substituents include, for example, alkyl groups, alkoxy groups and hydroxyl group. More preferred are methyl group, ethyl group and methoxy group. The heterocyclic ring represented by $Z_4$ is preferably a pyridinium ring, thiazolium ring and pyrimidinium ring. The heterocyclic ring represented by $Z_4$ may have a substituent. Preferred substituents include, for example, alkyl groups, halogen agons and alkoxy groups. Still preferred substituents are methyl group, ethyl group, chlorine atom and methoxy group. The alkyl groups $R_3$, $R_4$ and $R_5$ having 3 or less carbon atoms are preferably each methyl group or ethyl group. The inorganic anion $X_2$ is preferably a halide ion, more preferably chloride or iodide ion.

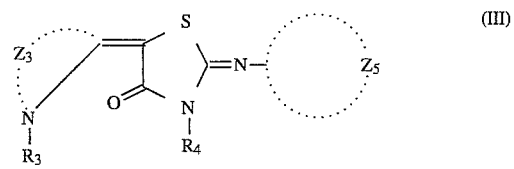

wherein $Z_3$, $R_3$ and $R_4$ are the same as those in the general formula (II), and $Z_5$ represents a non-metallic atom group necessitated for forming a pyridine ring, benzothiasole ring, naphthothiazole ring, quinoline ring or benzotriazole ring.

The heterocyclic ring $Z_3$ is preferably benzothiazoline ring, naphthothiazoline ring, thiasoline ring, thiazolidine ring or dihydroquinoline ring. It is most desirably the benzothiazoline ring.

The heterocyclic ring $Z_5$ is preferably pyridine ring, benzothiazole ring or benzotriazole ring.

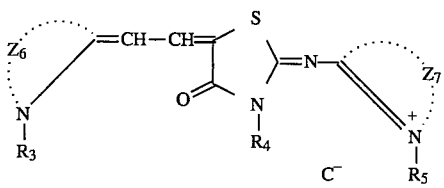

wherein $R_3$, $R_4$ and $R_5$ are the same as those in the general formula (II), and $Z_6$ represents a non-metallic atom group necessitated for forming a thiazolidine ring, thiazoline ring, benzothiazoline ring, tetrahydrobenzothiazoline ring, naphthothiazoline ring, dihydroquinoline ring or dihydropyridine ring.

The heterocyclic ring $Z_6$ is preferably thiazolidine ring, thiazoline ring, benzothiazoline ring, naphthothiazoline ring or dihydroquinoline ring.

$Z_7$ in the above formula represents a non-metallic atom group necessitated for forming a thiazolinium ring, thiazolium ring, benzothiazolium ring, naphthothiazolium ring, tetrahydrobenzothiazolium ring, pyridinium ring, quinolinium ring or pyrimidinium ring. $Z_7$ is preferably benzothiazolium ring, thiazolium ring or quinolium ring. The heterocyclic ring formed by $Z_6$ and $Z_7$ may have a substituent. Preferred substituents include alkyl groups, alkoxy groups and halogen atoms. More preferred are methyl, ethyl and methoxy groups.

The water-soluble methine compounds are preferably those represented by the general formula (V) or (VI):

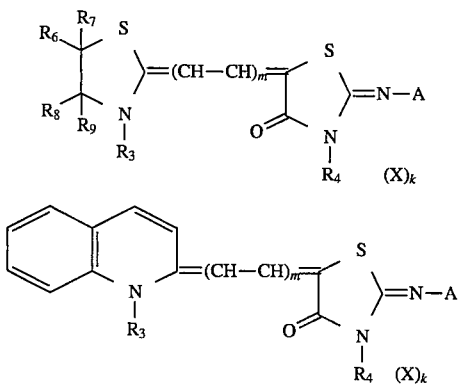

wherein A represents

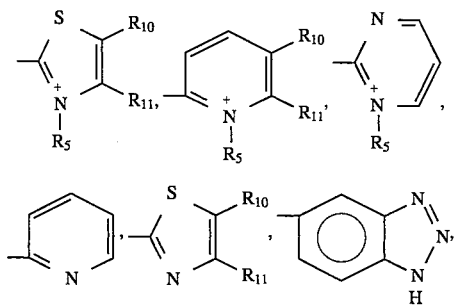

$R_6$, $R_7$, $R_8$ and $R_9$ together form a benzene ring or naphthalene ring, or $R_6$ and $R_7$ each represent a hydrogen or an alkyl group having 3 or less carbon atoms and $R_8$ and $R_9$ together form a single bond. $R_{10}$ and $R_{11}$ each represent a hydrogen atom or together form a benzene ring or naphthalene ring, $R_3$, $R_4$, $R_5$, k and X are as defined above, m represents 0 or 1, and the benzene ring and naphthalene ring may have a substituent; with the proviso that when m is 1, A is cationic, k is not zero and X represents chloride ion.

The methine compounds of the present invention are usable as spectral sensitizing dyes or antitumor agents such as anticancer agent. The methine compounds of the present invention can be usually easily synthesized with reference to synthesis methods described in U.S. Pat. No. 2,388,963.

Examples of the compounds of the general formula (I) according to the present invention will be given below, which by no means limit the invention.

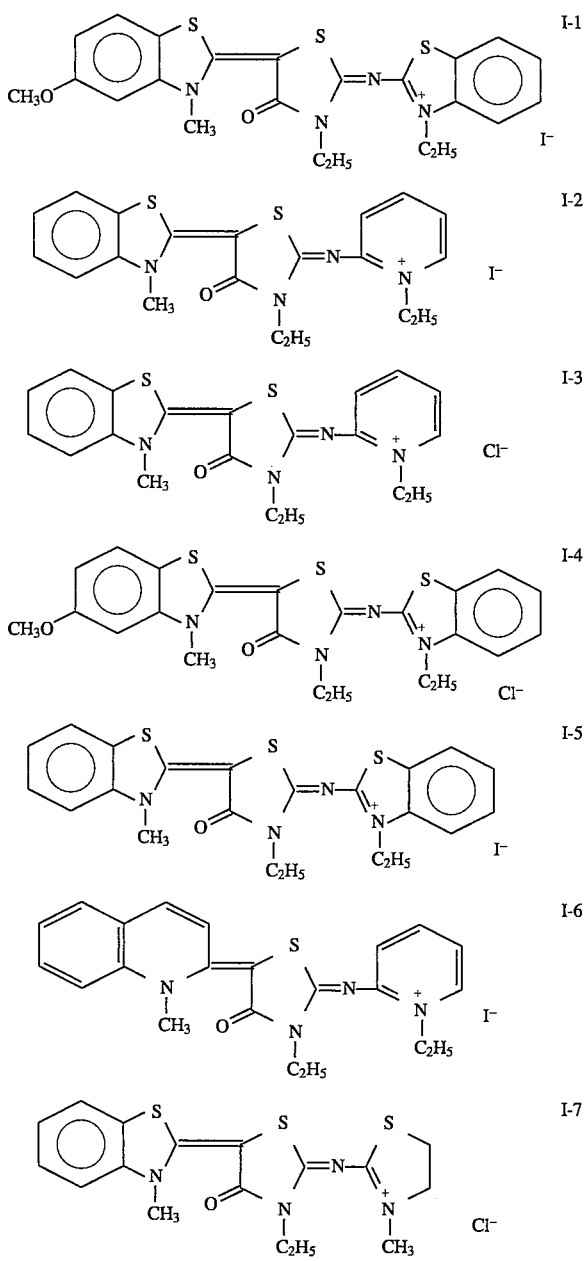

-continued

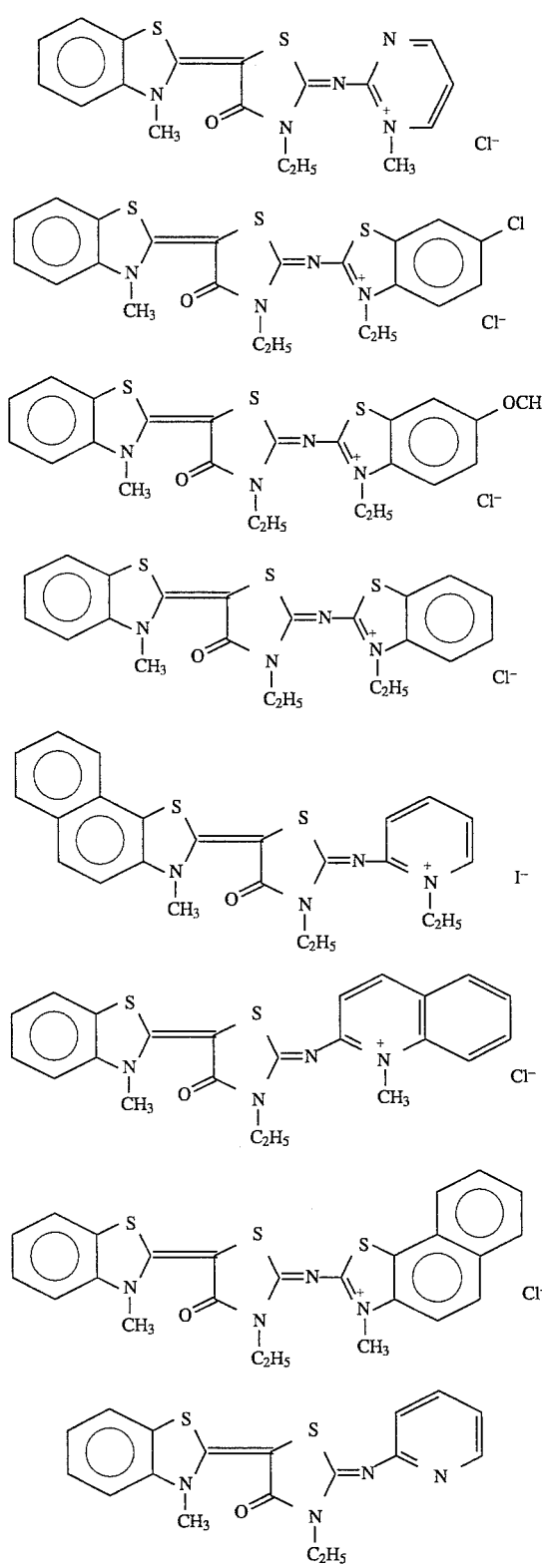

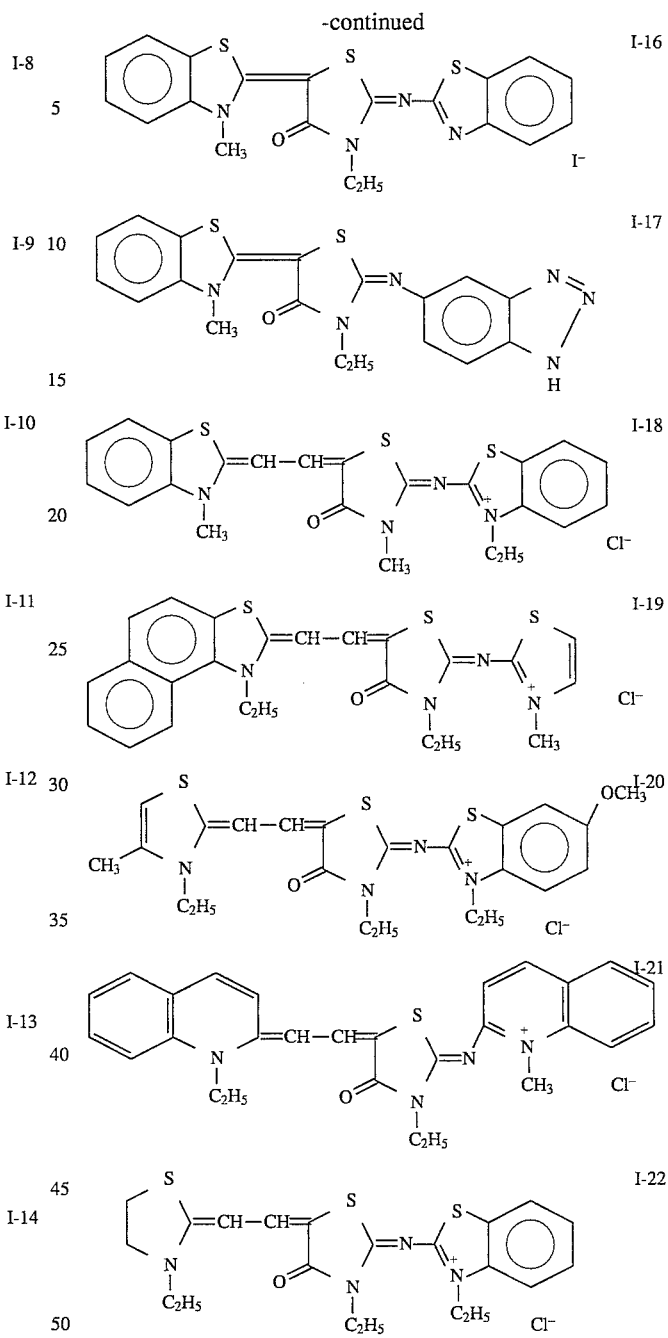

Since the methine compounds of the present invention have a color tone of a wavelength shorter than that of rhodacyanine dyes analogous to them and an extremely high solubility in water, it is expected to widely use them as short-wavelength spectral sensitizing dyes for photographic sensitive materials or as medicines such as antitumor agents.

The following Examples will further illustrate the effectiveness of the methine compounds of the formula (I) of the present invention.

EXAMPLE 1

(1) Synthesis of Compound I-2

1) Synthesis of 3-ethyl-5-(3-methylbenzothiazolin-2-ylidene)thiazoline-4-one-2-thione 400 g of 2-methylthiobenzothiazole, 616 g of methyl p-toluenesulfonate and 560 ml of anisole were fed into a 3 l three-necked flask provided with a reflux condenser. The resultant mixture was heated at 120° C. for 4 hours. The reaction mixture thus obtained was cooled to room temperature, 8 l of acetonitrile was added thereto and the resultant mixture was stirred at room temperature for 15 min. Then the mixture was transferred into a 10 l three-necked flask. 354 g of 3-ethylthiazoline-4-on-2-thion was added thereto and the mixture was cooled to 5° C. 0.5 l of triethylamine was added dropwise to the mixture at 10° C. for a period of 30 min. The resultant was stirred at 10° C. for 4 hours. The yellow precipitate thus obtained was suction-filtered and washed with 0.4 l of acetonitrile and then with 1.4 l of methanol to obtain 800 g of crude crystals.

The crude crystals, 2.1 l of acetone and 4.2 l of methanol were fed into a 10 l three-necked flask provided with a reflux condenser. The mixture was heated under reflux and stirring for 15 min and then cooled to 25° C. The resultant mixture was suction-filtered, washed with 1.4 l of methanol and dried.

Yield: 89.3 %.

2) Synthesis of 3-ethyl-5-(3-methylbenzothiazolin-2-ylidene)-2-methylthio-4-oxo-2-thiazolium p-toluenesulfonate 750 g of 3-ethyl-5-(3-methylbenzothiazolin-2-ylidene)thiazoline- 4-one-2-thione, 1360 g of methyl p-toluenesulfonate and 0.75 l of dimethylformamide were fed into a 10 l three-necked flask provided with a reflux condenser. The resultant mixture was heated at 130° C. under stirring for 2.5 hours. The reaction mixture thus obtained was cooled to 95° C. and 6.5 l of acetone was added thereto. Then the mixture was cooled to 25° C. The precipitates thus formed were suction-filtered and washed with 2 l of acetone.

The crude product and 5.2 l of acetone were fed into a 10 l three-necked flask provided with a reflux condenser. The mixture was heated under reflux and stirring for 15 min and then cooled to 25° C. The resultant precipitate was suction-filtered, washed with 2 l of acetone and dried.

Yield: 92.3 %.

3) Synthesis of 2-amino-1-ethylpyridinium iodide 28.2 g of 2-aminopyridine and 60.8 g of iodoethane were fed into a 1 l three-necked flask provided with a reflux condenser and they were heated under reflux for 2 hours. The reaction liquid was stirred at room temperature for additional 1 hour. Crystals thus formed were suction-filtered and washed with ethyl acetate (50 ml×2). The filtration residue was dried at room temperature under reduced pressure for 3 hours to obtain the intended compound.

Yield: 68.2 g.

4) Synthesis of 1-ethyl-2{[3-ethyl-5-(3-methylbenzothiazolin- 2-ylidene)]-4-oxothiazolidin-2-ylideneamino} pyridinium iodide (compound I-2)

24.7 g of 3-ethyl-5-(3-methylbenzothiazolin-2-ylidene)-2-methylthio-4-oxo-2-thiazolium p-toluenesulfonate, 12.5 g of 2-amino-1-ethylpyridinium iodide and 500 g of acetonitrile were fed into a 2 l three-necked flask and heated to an inner temperature of 50° C. under stirring. 20.2 g of triethylamine was added dropwise to the resultant solution and the obtained mixture was stirred at that temperature for 1.5 hours. The reaction liquid was cooled to room temperature, and the resultant crystals were suction-filtered and washed with acetonitrile (50 ml×2). The crude crystals thus obtained were dissolved in 250 ml of chloroform/methanol (1:1) under stirring. 400 ml of ethyl acetate was added to the solution to form crystals, which were then suction-filtered, washed with ethyl acetate (100 ml×2) and dried at room temperature under reduced pressure to obtain the intended compound.

Yield: 8.8 g, m.p.: 275° to 276° C.

(2) Synthesis of Compound I-3

1 g of compound I-2 was dissolved in 50 ml of chloroform/methanol (1/1l). The solution was passed through a column packed with a strongly basic ion exchange resin (Amberlyst A-26; a product of Japan Organo Co., Ltd.). After elution with methanol, the eluate was collected and filtered through a microfilter (0.2 μm), and the filtrate was concentrated under reduced pressure. The residue was dissolved in ether. Ethyl acetate was added to the solution to form crystals, which were suction-filtered, washed with ethyl acetate and dried at room temperature under reduced pressure to obtain the intended compound.

Yield: 0.8 g, m.p.: 242° to 244° C.

(3) Synthesis of Compound I-6

2.5 g of 3-ethyl-2-methylthio-5-(1-methylquinolin-2-ylidene)-4-oxo-2-thiazolium p-toluenesulfonate, 1.3 g of 2-amino-1-ethylpyridinium iodide and 50 ml of acetonitrile were fed into a 200 ml three-necked flask and they were heated to an internal temperature of 50° C. under stirring. 2.8 ml of triethylamine was added dropwise to the resultant solution and the obtained mixture was stirred at that temperature for additional 2 hours. Then the same procedure as that in the formation of compound I-2 was repeated to obtain compound I-6.

Yield: 1.2 g, m.p.: 233° to 234° C.

(4) Synthesis of Compound I-7

1) Synthesis of 2-amino-3-methylthiazolium p-toluenesulfonate:

2.0 g of 2-aminothiazole and 5.6 g of methyl p-toluenesulfonate were fed into a 200 ml three-necked flask and they were heated on an oil bath at 120° C. under stirring for 4 hours. The reaction mixture was cooled to 60° C., to which 100 ml of acetone was added. The resultant mixture was stirred for 1 hour. The resultant crystals were suction-filtered, washed with acetone and dried at room temperature under reduced pressure.

Yield: 5.4 g.

2) Synthesis of Compound I-7

2.5 g of 3-ethyl-5-(3-methylbenzothiazolin-2-ylidene)-2-methylthio-4-oxo-2-thiazolium p-tolunesulfonate, 1.4 g of 2-amino-3-methylthiazolium p-toluenesulfonate and 30 ml of acetonitrile were fed into a 200 ml three-necked flask and they were heated on a water bath at 60° C. under stirring. 2.2 ml of triethylamine was added dropwise to the solution and the resultant mixture was stirred at that temperature for 30 min. The reaction liquid was cooled to room temperature, and the resultant crystals were suction-filtered and washed with acetonitrile. The crude crystals thus obtained were dissolved in 50 ml of methylene chloride/methanol (1/1). 10 ml of acetonitrile was added to the solution and the resultant solution was concentrated under reduced pressure until the quantity of the solution was reduced to 1/5. The residue was left to stand at room temperature for 2 hours and the crystals thus formed were suction-filtered. The crystals were column-treated with a strongly basic ion exchange resin PA-318 (eluent: methanol) to obtain the intended compound.

Yield: 1.5 g, m.p.: 253° to 254° C.

(5) Synthesis of Compound I-8

1) Synthesis of 2-amino-1-methylpyrimidinium p-toluenesulfonate 1.8 g of 2-aminopyrimidine and 5.6 g of methyl p-toluenesulfonate were fed into a 200 ml three-necked flask and the mixture was stirred under heating on an oil bath at 120° C. for 3 hours. The reaction mixture was cooled to 60° C., to which 100 ml of acetone was added and the resultant mixture was stirred at room temperature for 1 hour. The crystals thus formed were suction-filtered, washed with acetone and dried at room temperature under reduced pressure.

Yield: 5.9 g.

2) Synthesis of Compound I-8

Compound I-8 was synthesized from 2.5 g of 3-ethyl-5-(3-methylbenzothiazolin-2-ylidene)-2-methylthio-4-oxo-2-thiazolium p-toluenesulfonate and 1.4 g of 2-amino-1-methylpyrimidinium p-toluenesulfonate in the same manner as that of the synthesis of compound I-7.

Yield: 1.8 g, m.p.: 248° to 250° C.

(6) Synthesis of Compound I-16

4.0 g of 3-Ethyl-5-(3-methylbenzothiazolin-2-ylidene)-2-methylthio-4-oxo-2-thiazolium p-toluenesulfonate, 1.5 g of 2-aminobenzothiazole and 50 ml of DMF were fed into a 200 ml three-necked flask. The resultant mixture was stirred under heating on an oil bath at 120° C. for 6 hours. The reaction liquid was left to stand at room temperature overnight. 50 ml of ethanol was added to the liquid to form crystals, which were suction-filtered. The crude crystals were recrystallized from chloroform/methanol twice to obtain the intended compound.

Yield: 1.9 g, m.p.: >300° C.

(7) Synthesis of Compound I-17

5.0 g of 3-ethyl-5-(3-methylbenzothiazolin-2-ylidene)-2-methylthio-4-oxo-2-thiazolium p-toluenesulfonate, 1.5 g of 5-aminobenzotriazole and 50 ml of DMF were fed into a 200 ml three-necked flask. The resultant mixture was stirred under heating on an oil bath at 140° C. for 6 hours. The reaction liquid was cooled, and 100 ml of methanol was added thereto to form crystals, which were suction-filtered. The crude crystals were purified according to silica gel column chromatography (chloroform/methanol) and then recrystallized from DMF/methanol three times to obtain the intended compound.

Yield: 1.6 g, m.p.: >300° C.

(8) Synthesis of Compound I-19

3.1 g of 3-ethyl-5-(3-ethylnaphtho[1,2-d]thiazolin-2-ylidene)-2-methylthio-4-oxo-2-thiazolium p-toluenesulfonate, 1.4 g of 2-amino-3-methylthiazolium p-toluenesulfonate and 30 ml of acetonitrile were fed into a 200 ml three-necked flask. The resultant mixture was stirred under heating on a water bath at 70° C. 2.2 ml of trimethylamine was added dropwise to the solution and the resultant mixture was stirred at that temperature for 1 hour. 100 ml of acetone was added to the reaction liquid and the thus-obtained mixture was stirred at room temperature for 1 hour. The crystals thus formed were suction-filtered and washed with acetone. The crude crystals were recrystallized from chloroform/methanol and then treated with a column packed with a strongly basic ion exchange resin (Diaion PA-318; a product of Mitsubishi Chemical Industries, Ltd.) to obtain the intended compound.

Yield: 1.1 g, m.p.: 229° to 231° C.

(9) Synthesis of Compound I-20

1) Synthesis of 2-amino-3-ethyl-6-methoxybenzothiazolium p-toluenesulfonate 3.6 g of 2-amino-6-methoxybenzothiazole and 6.0 g of ethyl p-toluenesulfonate were fed into a 200 ml three-necked flask. The resultant mixture was stirred under heating on an oil bath at 120° C. for 3 hours. Acetone was added to the reaction mixture and the resultant mixture was stirred at room temperature for 1 hour. The crystals thus formed were suction-filtered and washed with acetone to obtain the intended compound.

Yield: 6.3 g.

2) Synthesis of Compound I-20

1.50 g of 3-ethyl-5-{2-(3-ethyl-4-methylthiazolin-2-ylidene) ethylidene}-3-methylthio-4-oxo-thiazolium p-toluenesulfonate, 1.14 g of 2-amino-3-ethyl-6-methoxybenzothiazolium p-toluenesulfonate and 18 ml of acetonitrile were fed into a 200 ml three-necked flask. The resultant mixture was stirred under heating on a water bath at 70° C. for 2.5 hours. 50 ml of acetone and 50 ml of ethyl acetate were added to the reaction liquid and the resultant mixture was stirred for 1 hour. The crystals thus formed were suction-filtered and washed with ethyl acetate. The crystals were recrystallized from chloroform/methanol and then treated with a column packed with a strongly basic ion exchange resin (Diaion PA-318; a product of Mitsubishi Chemical Industries, Ltd.) to obtain the intended compound.

Yield: 0.3 g, m.p.: 170° to 173° C.

Other compounds listed above could be synthesized in the same manner as that described above. The melting points and NMR data of them are given in Tables 1 to 5.

TABLE 1

| Compound No. | M.p. [°C.] | NMR chemical shift TMS standard | DMSO-$d_6$ |
|---|---|---|---|
| I-1 | 261–263 | δ8.26(1H, d, 8.0Hz), 8.05(1H, d, 8.0Hz), 7.85(1H, d, 8.0Hz), 7.76(1H, t, 8.0Hz), 7.58(1H, d, 8.0Hz), 7.35(1H, d, 1.0Hz), 6.93(1H, dd, 8.0Hz, 1.0Hz), 4.60(2H, q, 6.7Hz), 4.20(3H, s), 3.80(3H, s), 1.43(3H, t, 6.7Hz), 1.33(3H, t, 6.7Hz) | |
| I-2 | 275–276 | δ8.85(1H, d, 8.0Hz), 8.40(1H, t, 8.0Hz), 7.95(2H, d, 8.0Hz), 7.70–7.45(3H, m), 7.36(1H, t, 8.0Hz), 4.53(2H, q, 6.7Hz), 4.03(2H, q, 6.7Hz), 3,97(3H, s), 1.43(3H, t, 6.7Hz), 1.30(3H, t, 6.7Hz) | |
| I-3 | 242–244 | δ8.85(1H, d, 8.0Hz), 8.40(1H, t, 8.0Hz), 7.95(2H, d, 8.0Hz), 7.70–7.45(3H, m), 7.36(1H, t, 8.0Hz), 4.53(2H, q, 6.7Hz), 4.03(2H, q, 6.7Hz), 3,97(3H, s), 1.43(3H, t, 6.7Hz), 1.30(3H, t, 6.7Hz) | |
| I-4 | 249–250 | δ8.26 (1H, d, 8.0Hz), 8.05(1H, d, 8.0Hz), 7.85(1H, d, 8.0Hz), 7.76(1H, t, 8.0Hz), 7.58(1H, d, 8.0Hz), 7.35(1H, d, 1.0Hz), 6.93(1H, dd, 8.0Hz, 1.0Hz), 4.60(2H, q, 6.7Hz), 4.20(3H, s), 3.80(3H, s), 1.43(3H, t, 6.7Hz), 1.33(3H, t, 6.7Hz) | |

TABLE 2

| Compound No. | M.p. [°C.] | NMR chemical shift TMS standard DMSO-$d_6$ |
|---|---|---|
| I-5 | 257–259 | δ8.26(1H, d, 8.0Hz), 8.03(1H, t, 8.0Hz), 7.76(2H, δ, 8.0Hz), 7.56(2H, q, 8.0Hz), 7.37(1H, t, 8.0Hz), 4.64 (2H, q, 6.7Hz), 4.22(3H, s), 1.43(3H, t, 6.7Hz), 1.35(3H, t, 6.7Hz) |
| I-6 | 233–234 | δ8.78(1H, d, 8.0Hz), 8.35(1H, t, 8.0Hz), 7.96(2H, t, 8.0Hz), 7.88–7.70(4H, m), 7.57(2H, m), 4.52(2H, q, 6.7Hz), 4.03(2H, q, 6.7Hz), 3.94(3H, s), 1.42(3H, t, 6.7Hz), 1.26(3H, t, 6.7Hz) |
| I-7 | 253–254 | δ8.05(1H, d, 4.0Hz), 7.98(1H, d, 8.0Hz), 7.80(1H, d, 4.0Hz), 7.75(1H, d, 8.0Hz), 7.56(1H, t, 8.0Hz), 7.48(1H, t, 8.0Hz), 4.13(3H, s), 4.10(2H, q, 6.7Hz), 3.90(3H, s), 1.30(3H, t, 6.7Hz) |
| I-8 | 248–250 | δ9.23(1H, dd, 4.0Hz, 1.0Hz), 9.05(1H, dd, 6.7Hz, 4.0Hz), 7.97(1H, d, 8.0Hz), 7.70(1H, d, 8.0Hz), 7.55(1H, t, 8.0Hz), 7.50(1H, t, 8.0Hz), 7.36(1H, t, 8.0Hz), 4.17(2H, q, 6.7Hz), 4.12(3H, s), 4.04(3H, s), 1.33(3H, t, 6.7Hz) |
| I-9 | 254–256 | δ8.38(1H, d, 1.0Hz), 8.06(2H, t, 8.0Hz), 7.83(2H, d, 8.0Hz), 7.59(1H, t, 8.0Hz), 7.43(1H, t, 8.0Hz), 4.63(2H, q, 6.7Hz), 4.20(2H, q, 6.7Hz), 4.19(3H, s), 1.42(3H, t, 6.7Hz), 1.34(3H, t, 6.7Hz) |

TABLE 3

| Compound No. | M.p. [°C.] | NMR chemical shift TMS standard DMSO-$d_6$ |
|---|---|---|
| I-10 | 216–218 | δ8.00(1H, s), 7.96(1H, d, 1.0Hz), 7.80(1H, d, 8.0Hz), 7.55(1H, t, 8.0Hz), 7.35(2H, t, 8.0Hz), 4.60(2H, q, 6.7Hz), 4.15(2H, q, 6.7Hz), 4,15(3H, s), 3.84(3H, s), 1.40(3H, t, 6.7Hz), 1.33(3H, t, 6.7Hz) |
| I-11 | 224–225 | 8.26(1H, d, 8.0Hz), 8.03(1H, t, 8.0Hz), 7.76(2H, q, 8.0Hz), 7.56(2H, q, 8.0Hz), 7.37(1H, t, 8.0Hz), 4.64(2H, q, 6.7Hz), 4.22(3H, s), 1.43(3H, t, 6.7Hz), 1.35(3H, t, 6.7Hz) |
| I-12 | 268–269 | δ8.80(1H, d, 8.0Hz), 8.48(1H, t, 8.0Hz), 8.15–8.05(2H, m), 8.00–7.80(3H, m), 7.16(1H, t, 8.0Hz), 7.60–7.50(2H, m), 4.51(2H, q, 6.7Hz), 4.05(3H, s), 4.00(2H, q, 6.7Hz), 1.43(3H, t, 6.7Hz), 1.27(3H, t, 6.7Hz) |
| I-13 | 256–257 | δ8.83(1H, d, 8.0Hz), 8.27(2H, t, 8.0Hz), 8.10(1H, d, 8.0Hz), 7.98(2H, t, 8.0Hz), 7.80(1H, t, 8.0Hz), 7.68(1H, d, 8.0Hz), 7.54(1H, t, 8.0Hz), 7.36(1H, t, 8.0Hz), 7.27(3H, s), 4.10(2H, q, 6.7Hz), 4.00(3H, s), 1.37(3H, t, 6.7Hz) |

TABLE 4

| Compound No. | M.p. [°C.] | NMR chemical shift TMS standard DMSO-$d_6$ |
|---|---|---|
| I-14 | 219–221 | δ8.34(2H, dd, 8.0Hz, 1.0Hz), 8.20(2H, t, 8.0Hz), 8.05(1H, d, 8.0Hz), 7.87(1H, d, 8.0Hz), 7.82(1H, d, 8.0Hz), 7.70(1H, t, 8.0Hz), 7.55(1H, t, 8.0Hz), 7.40(1H, t, 8.0Hz), 4.27(3H, s), 4.25(2H, q, 6.7Hz), 4.16(3H, s), 1.48(3H, t, 6.7Hz) |
| I-15 | 269–270 | δ8.55–8.45(1H, m), 7.70(1H, t, 8.0Hz), 7.56(1H, d, 8.0Hz), 7.38(1H, t, 8.0Hz), 7.30–7.10(3H, m), 7.05–6.93(1H, m), 4.20(2H, q, 6.7Hz), 4.00(3H, s), 1.38(3H, t, 6.7Hz) |
| I-16 | >300 | δ7.90(1H, d, 8.0Hz), 7.77(1H, d, 8.0Hz), 7.63(1H, d, 8.0Hz), 7.50–7.35(2H, m), 7.32–7.16(3H, m), 4.18(2H, q, 6.7Hz), 4.06(3H, s), 1.40(3H, t, 6.7Hz) |
| I-17 | >300 | δ8.04–7.90(1H, m), 7.75(1H, d, 8.0Hz), 7.47–7.33(3H, m), 7.30–7.16(1H, m), 7.12(1H, m), 3.96(2H, q, 6.7Hz), 3.74(3H, s), 1.30(3H, t, 6.7Hz) |
| I-18 | 206–207 | δ8.27(1H, d, 8.0Hz), 8.05(1H, d, 8.0Hz), 8.02–7.40(6H, m), 7.40–7.25(1H, m), 6.13(1H, d, 13.0Hz), 4.66(2H, q, 6.7Hz), 3.80(3H, s), 3.46(3H, s), 1.44(3H, t, 6.7Hz) |

TABLE 5

| Compound No. | M.p. [°C.] | NMR chemical shift TMS standard DMSO-$d_6$ |
|---|---|---|
| I-19 | 229–231 | δ8.42(1H, d, 8.0Hz), 8.12–7.53(7H, m), 6.12(1H, d, 13.0Hz), 4.86–4.52(2H, m), 3.84(3H, s), 3.78(2H, q, 6.7Hz), 1.67(3H, t, 6.7Hz), 1.18(3H, t, 6.7Hz) |
| I-20 | 170–173 | δ7.97(1H, d, 8.0Hz), 7.87(1H, d, 1.3Hz), 7.80(1H, d, 13.0Hz), 7.35(1H, dd, 8.0Hz, 1.3Hz), 7.05(1H, s), 6.05(1H, d, 13.0Hz), 4.60(2H, q, 6.7Hz), 4.20(2H, q, 6.7Hz), 4.06(2H, q, 6.7Hz), 3.87(3H, s), 2.34(3H, s), 1.40(3H, t, 6.7Hz), 1.27(3H, t, 6.7Hz) |
| I-21 | 240–241 | δ8.88(1H, d, 8.0Hz), 8.37–7.90(5H, m), 7.90–7.57(6H, m), 7.34(1H, t, 8.0Hz), 5.45(1H, d, 13.0Hz), 4.27(3H, s), 4.27(2H, q, 6.7Hz), 1.30(3H, t, 6.7Hz), 1.26(3H, t, 6.7Hz) |
| I-22 | 161–163 | δ8.30(1H, d, 8.0Hz), 8.12(1H, d, 8.0Hz), 7.85–7.55(3H, m), 5.80(1H, d, 13.0Hz), 4.66(2H, q, 6.7Hz), 4.13(4H, m), 3.71(2H, q, 6.7Hz), 3.43(2H, q, 6.7Hz), 1.43(3H, t, 6.7Hz), 1.30(3H, t, 6.7Hz), 1.23(3H, t, 6.7Hz) |

EXAMPLE 2

The absorption spectrum of each of the compounds of the present invention synthesized in Example 1 and dissolved in methanol was determined. The maximum absorption wavelength and molar extinction coefficient of each compound are given in Tables 6 and 7.

Comparative Compounds:

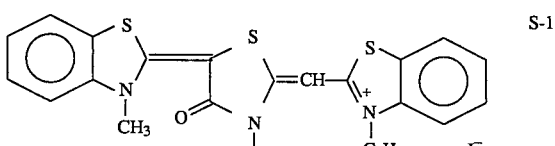

S-1

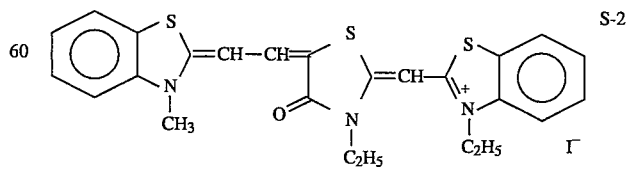

S-2

TABLE 6

| Compound No. | MeOH λ[nm] max | ε |
|---|---|---|
| S-1 (Comp. Ex.) | 500 | $7.49 \times 10^4$ |
| I-1 (present invention) | 460 | $4.45 \times 10^4$ |
| I-2 (present invention) | 434 | $3.52 \times 10^4$ |
| I-3 (present invention) | 435 | $3.37 \times 10^4$ |
| I-4 (present invention) | 467 | $4.50 \times 10^4$ |
| I-5 (present invention) | 460 | $4.87 \times 10^4$ |
| I-6 (present invention) | 479 | $3.84 \times 10^4$ |
| I-7 (present invention) | 444 | $3.55 \times 10^4$ |
| I-8 (present invention) | 441 | $3.59 \times 10^4$ |
| I-9 (present invention) | 462 | $4.17 \times 10^4$ |
| I-10 (present invention) | 466 | $4.74 \times 10^4$ |
| I-11 (present invention) | 459 | $4.65 \times 10^4$ |

TABLE 7

| Compound No. | MeOH λ[nm] max | ε |
|---|---|---|
| I-12 (present invention) | 446 | $4.01 \times 10^4$ |
| I-13 (present invention) | 464 | $3.02 \times 10^4$ |
| I-14 (present invention) | 470 | $4.44 \times 10^4$ |
| I-15 (present invention) | 412 | $6.39 \times 10^4$ |
| I-16 (present invention) | 428 | $6.97 \times 10^4$ |
| I-17 (present invention) | 388 | $4.83 \times 10^4$ |
| S-2 (Comp. Ex.) | 593 | $9.44 \times 10^4$ |
| I-18 (present invention) | 564 | $7.58 \times 10^4$ |
| I-19 (present invention) | 570 | $8.31 \times 10^4$ |
| I-20 (present invention) | 570 | $5.93 \times 10^4$ |
| I-21 (present invention) | 582 | $5.80 \times 10^4$ |
| I-22 (present invention) | 520 | $5.78 \times 10^4$ |

It will be apparent from the above table that the wavelengths of the methine compounds of the present invention are shorter than those of the ordinary rhodacyanines.

EXAMPLE 3

The solubility tests of the compounds of the present invention synthesized in Example 1 were conducted.
Solubility Experiment Conditions: 10 mg of a compound to be examined was fed into a test tube. 0.1 ml of ion-exchanged water was added to the compound and the resultant mixture was shaken at room temperature for 3 min to macroscopically evaluate the solubility.
Comparative Compounds:
The following compounds S-3 to S-5 were used as the comparative compounds in addition to the above-mentioned compounds S-1 and S-2.

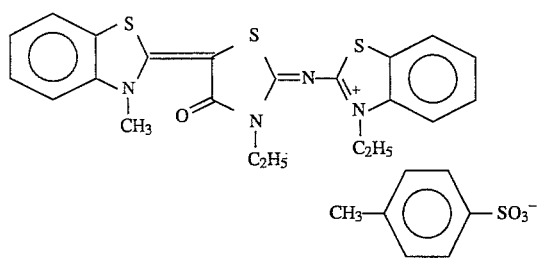

S-3

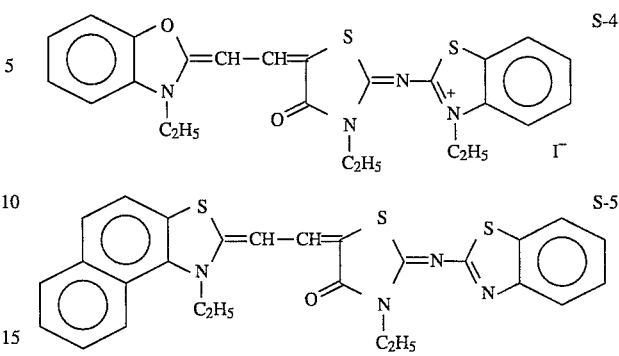

S-4

S-5

In the above-described dissolution tests, all of the compounds I-1 to I-22 of the present invention were dissolved, while any of the comparative compounds S-1 to S-5 was not dissolved.

It is apparent from these results that the methine compounds of the present invention have a shorter-wavelength color tone and far higher solubility than those of the ordinary rhodacyanine dyes.

What is claimed is:

1. A methine compound represented by the following formula (V):

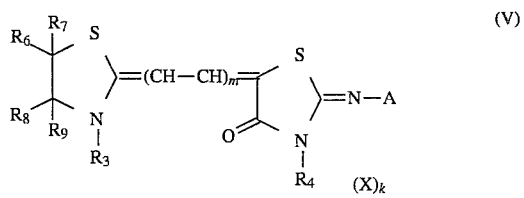

(V)

wherein A represents

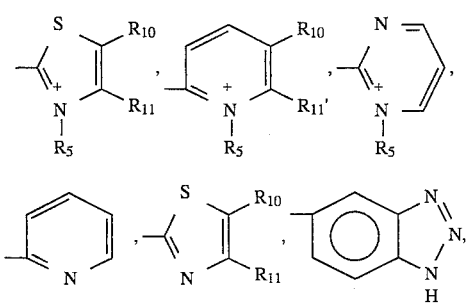

wherein $R_3$, $R_4$ and $R_5$ each represent an alkyl group having 3 or less carbon atoms; $R_6$, $R_7$, $R_8$ and $R_9$ together form a benzene ring or a naphthalene ring, or $R_6$ and $R_8$ each represent a hydrogen atom or an alkyl group having 3 or less carbon atoms and $R_7$ and $R_9$ together form a single bond; x represents a halogen anion; k represents a number necessitated for adjusting the electric charge of the molecule to zero; and m represents 0 or 1; with the proviso that when m is 1, A is cationic, k is not zero and X represents a chloride ion.

2. The methine compound according to claim 1, wherein A represents

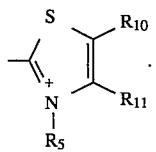

3. The methine compound according to claim 1, wherein A represents

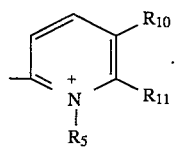

4. The methine compound according to claim 1, wherein A represents

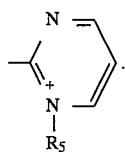

5. The methine compound according to claim 1, wherein A represents

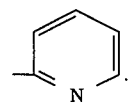

6. The methine compound according to claim 1, wherein A represents

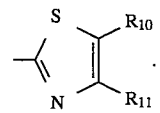

7. The methine compound according to claim 1, wherein A represents

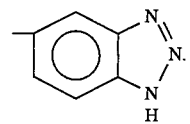

* * * * *

UNITED STATES PATENT AND TRADEMARK OFFICE
CERTIFICATE OF CORRECTION

PATENT NO. : 5,476,945
DATED : December 19, 1995
INVENTOR(S) : Akihiko Ikegawa et al It is certified that error appears in the above-identified patent and that said Letters Patent is hereby corrected as shown below:

On the cover page, left column, section [30],
  delete "4-304769" and insert therefor --4-305769--.

On the cover page, right column, section [57] ABSTRACT, delete

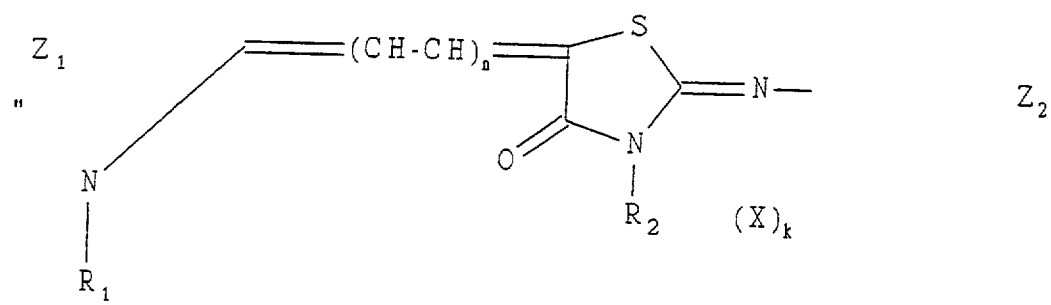

and insert therefor

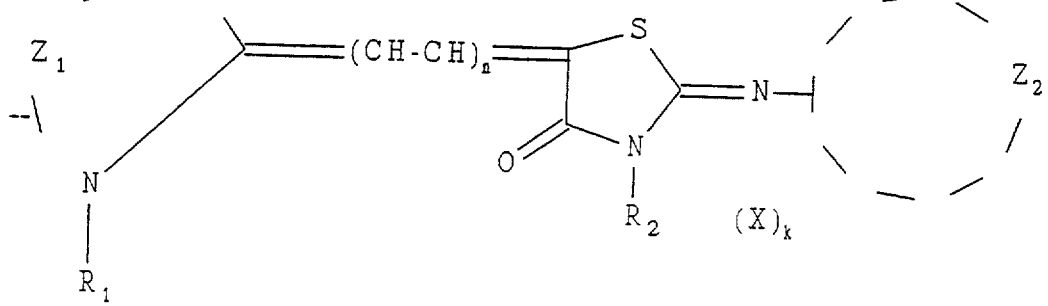

UNITED STATES PATENT AND TRADEMARK OFFICE
CERTIFICATE OF CORRECTION

PATENT NO. : 5,476,945

DATED : December 19, 1995

INVENTOR(S) : Akihiko Ikegawa et al

It is certified that error appears in the above-identified patent and that said Letters Patent is hereby corrected as shown below:

Column 2, line 65, change "thiasoline" and insert therefor --thiazoline--.

Column 14, line 62, after "ion" insert --; $R_{10}$ and $R_{11}$ each represent a hydrogen atom or together form a benzene ring or naphthalene ring--.

Signed and Sealed this

Twenty-seventh Day of August, 1996

Attest:

BRUCE LEHMAN

Attesting Officer    Commissioner of Patents and Trademarks